(12) United States Patent
Rosenquist et al.

(10) Patent No.: US 8,162,013 B2
(45) Date of Patent: Apr. 24, 2012

(54) CONNECTORS FOR FLUID CONTAINERS (76) Inventors: Tobias Rosenquist, Kallered (SE);
Johanna Lindstrom, Askim (SE);
Alexander Cederschiold, Gothenburg
(SE); Jonas Leffler, Gothenburg (SE)

( * ) Notice: Subject to any disclaimer, the term of this patent is extended or adjusted under 35 U.S.C. 154(b) by 155 days.

(21) Appl. No.: 12/784,985

(22) Filed: May 21, 2010

(65) Prior Publication Data

US 2011/0284561 A1 Nov. 24, 2011

(51) Int. Cl.
*A61M 39/00* (2006.01)
*A61J 1/00* (2006.01)
(52) U.S. Cl. .......... 141/384; 141/383; 141/346; 285/86; 604/415
(58) Field of Classification Search ............ 141/311 R, 141/313, 346, 367, 383, 384; 285/91, 92, 285/85, 86; 604/411, 414, 415
See application file for complete search history.

(56) References Cited

U.S. PATENT DOCUMENTS

| | | | |
|---|---|---|---|
| 1,844,342 A | 2/1932 | Berman |
| 2,010,417 A | 8/1935 | Schwab |
| 2,697,438 A | 12/1954 | Hickey |
| 2,717,599 A | 9/1955 | Huber |
| 3,064,651 A | 11/1962 | Henderson |
| 3,071,135 A | 1/1963 | Baldwin et al. |
| 3,308,822 A | 3/1967 | DeLuca |
| 3,316,908 A | 5/1967 | Burke |
| 3,340,671 A | 9/1967 | Loo |
| 3,390,677 A | 7/1968 | Razimbaud |
| 3,448,740 A | 6/1969 | Figge |
| 3,542,240 A | 11/1970 | Solowey |
| 3,783,895 A | 1/1974 | Weichselbaum |
| 3,788,320 A | 1/1974 | Dye |
| 3,822,700 A | 7/1974 | Pennington |
| 3,938,520 A | 2/1976 | Scislowicz et al. |
| 3,976,073 A | 8/1976 | Quick et al. |
| 4,096,860 A | 6/1978 | McLaughlin |

(Continued)

FOREIGN PATENT DOCUMENTS

AU 200112863 5/2003

(Continued)

OTHER PUBLICATIONS

Taiwan Search Report for Taiwan Patent Application 092106323 dated Mar. 21, 2003 (4 pages).

(Continued)

*Primary Examiner* — Timothy L Maust
*Assistant Examiner* — Timothy Kelly
(74) *Attorney, Agent, or Firm* — Diehl Servilla LLC (57) ABSTRACT

This document provides connectors such as a connector for enabling fluid transfer between a first fluid container and a second fluid container, which connector comprises a first component that is arranged to be connected to a first fluid container and a second component that is arranged to be connected to a second fluid container. The first component can be non-rotatably connected to the second component before a second fluid container is connected to the second component and/or before a first fluid container is connected to the first component. The connector can comprise a locking and rotation-enabling element that is arranged to be activated once a second fluid container has been connected to the second component, and/or once a first fluid container has been connected to the first component, which locking and rotation-enabling element enables the first component and the second component to rotate freely with respect to one another.

15 Claims, 7 Drawing Sheets

U.S. PATENT DOCUMENTS

| | | | |
|---|---|---|---|
| 4,296,786 A | 10/1981 | Brignola | |
| D270,568 S | 9/1983 | Armstrong | |
| 4,490,139 A | 12/1984 | Huizenga et al. | |
| 4,516,967 A | 5/1985 | Kopfer | |
| 4,564,054 A | 1/1986 | Gustavsson | |
| 4,573,967 A | 3/1986 | Hargrove et al. | |
| 4,576,211 A | 3/1986 | Valentini et al. | |
| 4,581,016 A | 4/1986 | Gettig | |
| 4,582,223 A | 4/1986 | Kobe | |
| 4,588,403 A | 5/1986 | Weiss et al. | |
| 4,600,040 A | 7/1986 | Naslund | |
| 4,623,343 A | 11/1986 | Thompson | |
| 4,629,455 A | 12/1986 | Kanno | |
| 4,632,673 A | 12/1986 | Tiitola et al. | |
| 4,636,204 A | 1/1987 | Christopherson et al. | |
| 4,673,010 A * | 6/1987 | Prufer et al. | 141/382 |
| 4,673,400 A | 6/1987 | Martin | |
| 4,673,404 A | 6/1987 | Gustavsson | |
| 4,737,150 A | 4/1988 | Baeumle et al. | |
| 4,752,287 A | 6/1988 | Kurtz et al. | |
| 4,759,756 A | 7/1988 | Forman et al. | |
| 4,768,568 A | 9/1988 | Fournier et al. | |
| 4,792,329 A | 12/1988 | Schreuder | |
| 4,804,015 A | 2/1989 | Albinsson | |
| 4,822,340 A | 4/1989 | Kamstra | |
| 4,826,492 A | 5/1989 | Magasi | |
| 4,834,717 A | 5/1989 | Haber et al. | |
| 4,842,585 A | 6/1989 | Witt | |
| 4,850,978 A | 7/1989 | Dudar et al. | |
| 4,864,717 A | 9/1989 | Baus, Jr. | |
| 4,872,494 A | 10/1989 | Coccia | |
| 4,878,897 A | 11/1989 | Katzin | |
| 4,889,529 A | 12/1989 | Haindl | |
| 4,898,209 A | 2/1990 | Zbed | |
| 4,909,290 A | 3/1990 | Coccia | |
| 4,932,937 A | 6/1990 | Gustavsson et al. | |
| 4,944,736 A | 7/1990 | Holtz | |
| 4,964,855 A | 10/1990 | Todd et al. | |
| 4,982,769 A | 1/1991 | Fournier et al. | |
| 4,994,048 A | 2/1991 | Metzger | |
| 4,997,083 A | 3/1991 | Loretti et al. | |
| 5,017,186 A | 5/1991 | Arnold | |
| 5,041,105 A | 8/1991 | D'Alo et al. | |
| 5,061,264 A | 10/1991 | Scarrow | |
| 5,071,413 A | 12/1991 | Utterberg | |
| 5,122,116 A | 6/1992 | Kriesel et al. | |
| 5,122,123 A | 6/1992 | Vaillancourt | |
| 5,137,524 A | 8/1992 | Lynn et al. | |
| 5,158,554 A | 10/1992 | Jepson et al. | |
| 5,176,673 A | 1/1993 | Marrucchi | |
| 5,199,947 A | 4/1993 | Lopez et al. | |
| 5,201,725 A | 4/1993 | Kling | |
| 5,207,658 A | 5/1993 | Rosen et al. | |
| 5,232,109 A | 8/1993 | Tirrell et al. | |
| 5,254,097 A | 10/1993 | Schock et al. | |
| 5,279,576 A | 1/1994 | Loo et al. | |
| 5,279,583 A | 1/1994 | Shober, Jr. et al. | |
| 5,279,605 A | 1/1994 | Karrasch et al. | |
| 5,308,347 A | 5/1994 | Sunago et al. | |
| 5,312,366 A | 5/1994 | Vaillancourt | |
| 5,328,480 A | 7/1994 | Melker et al. | |
| 5,334,163 A | 8/1994 | Sinnett | |
| 5,356,406 A | 10/1994 | Schraga | |
| 5,385,545 A | 1/1995 | Kriesel et al. | |
| 5,385,547 A | 1/1995 | Wong et al. | |
| 5,389,085 A | 2/1995 | D'Alessio et al. | |
| 5,405,326 A | 4/1995 | Haber et al. | |
| 5,445,630 A | 8/1995 | Richmond | |
| 5,447,501 A | 9/1995 | Karlsson et al. | |
| 5,456,675 A | 10/1995 | Wolbring et al. | |
| 5,470,522 A | 11/1995 | Thome et al. | |
| 5,478,328 A | 12/1995 | Silverman et al. | |
| 5,478,337 A | 12/1995 | Okamoto et al. | |
| 5,492,531 A | 2/1996 | Post et al. | |
| 5,514,117 A | 5/1996 | Lynn | |
| 5,515,871 A | 5/1996 | Bittner et al. | |
| 5,536,259 A | 7/1996 | Utterberg | |
| 5,575,780 A | 11/1996 | Saito | |
| 5,593,028 A | 1/1997 | Haber et al. | |
| 5,613,954 A | 3/1997 | Nelson et al. | |
| 5,632,735 A | 5/1997 | Wyatt et al. | |
| 5,647,845 A | 7/1997 | Haber et al. | |
| 5,685,866 A | 11/1997 | Lopez | |
| 5,752,942 A | 5/1998 | Doyle et al. | |
| 5,766,147 A | 6/1998 | Sancoff et al. | |
| 5,766,211 A | 6/1998 | Wood et al. | |
| 5,782,872 A | 7/1998 | Muller | |
| 5,795,336 A | 8/1998 | Romano et al. | |
| 5,817,083 A | 10/1998 | Shemesh et al. | |
| 5,820,609 A | 10/1998 | Saito | |
| 5,827,262 A | 10/1998 | Neftel et al. | |
| 5,837,262 A | 11/1998 | Golubev et al. | |
| 5,875,931 A | 3/1999 | Py | |
| 5,879,345 A | 3/1999 | Aneas | |
| 5,897,526 A | 4/1999 | Vaillancourt | |
| 5,934,510 A | 8/1999 | Anderson | |
| 5,984,899 A | 11/1999 | D'Alessio et al. | |
| 6,063,068 A | 5/2000 | Fowles et al. | |
| D427,308 S | 6/2000 | Zinger | |
| 6,070,623 A | 6/2000 | Aneas | |
| 6,071,270 A | 6/2000 | Fowles et al. | |
| 6,090,091 A | 7/2000 | Fowles et al. | |
| 6,113,068 A | 9/2000 | Ryan | |
| 6,113,583 A | 9/2000 | Fowles et al. | |
| 6,142,446 A | 11/2000 | Leinsing | |
| 6,146,362 A | 11/2000 | Turnbull et al. | |
| 6,209,738 B1 | 4/2001 | Jansen et al. | |
| 6,221,065 B1 | 4/2001 | Davis | |
| 6,245,056 B1 | 6/2001 | Walker et al. | |
| D445,501 S | 7/2001 | Niedospial, Jr. | |
| 6,253,804 B1 | 7/2001 | Safabash | |
| 6,258,078 B1 | 7/2001 | Thilly | |
| 6,293,595 B1 * | 9/2001 | Marc et al. | 285/92 |
| 6,387,074 B1 | 5/2002 | Horppu et al. | |
| 6,453,956 B2 | 9/2002 | Safabash | |
| 6,471,674 B1 | 10/2002 | Emig et al. | |
| 6,517,523 B1 | 2/2003 | Kaneko et al. | |
| 6,537,263 B1 | 3/2003 | Aneas | |
| 6,571,837 B2 | 6/2003 | Jansen et al. | |
| 6,591,876 B2 | 7/2003 | Safabash | |
| 6,644,367 B1 | 11/2003 | Savage et al. | |
| 6,685,692 B2 | 2/2004 | Fathallah | |
| 6,715,520 B2 | 4/2004 | Andreasson et al. | |
| 6,761,286 B2 | 7/2004 | Py et al. | |
| D495,416 S | 8/2004 | Dimeo et al. | |
| 6,786,244 B1 | 9/2004 | Jones | |
| D506,256 S | 6/2005 | Miyoshi et al. | |
| 6,960,194 B2 | 11/2005 | Hommann et al. | |
| 7,000,806 B2 | 2/2006 | Py et al. | |
| 7,080,672 B2 | 7/2006 | Fournier et al. | |
| 7,281,947 B2 * | 10/2007 | Pescatore | 439/578 |
| 7,297,140 B2 | 11/2007 | Orlu et al. | |
| D570,477 S | 6/2008 | Gallogly et al. | |
| D572,820 S | 7/2008 | Gallogly et al. | |
| D577,438 S | 9/2008 | Gallogly et al. | |
| D577,822 S | 9/2008 | Gallogly et al. | |
| D582,033 S | 12/2008 | Baxter et al. | |
| D605,755 S | 12/2009 | Baxter et al. | |
| 7,703,486 B2 | 4/2010 | Costanzo | |
| D616,984 S | 6/2010 | Gilboa | |
| 7,744,581 B2 | 6/2010 | Wallen et al. | |
| 7,975,733 B2 * | 7/2011 | Horppu et al. | 141/330 |
| 2001/0021825 A1 | 9/2001 | Becker et al. | |
| 2001/0025671 A1 | 10/2001 | Safabash | |
| 2002/0002352 A1 | 1/2002 | Becker et al. | |
| 2002/0082586 A1 | 6/2002 | Finley et al. | |
| 2002/0127150 A1 | 9/2002 | Sasso | |
| 2002/0177819 A1 | 11/2002 | Barker et al. | |
| 2003/0010717 A1 | 1/2003 | Brugger et al. | |
| 2003/0070726 A1 | 4/2003 | Andreasson et al. | |
| 2003/0106610 A1 | 6/2003 | Roos et al. | |
| 2003/0107628 A1 | 6/2003 | Fowles et al. | |
| 2003/0199846 A1 | 10/2003 | Fowles et al. | |
| 2003/0233083 A1 | 12/2003 | Houwaert et al. | |
| 2004/0116858 A1 | 6/2004 | Heinz et al. | |
| 2004/0199139 A1 | 10/2004 | Fowles et al. | |
| 2004/0215147 A1 | 10/2004 | Wessman et al. | |

| | | | |
|---|---|---|---|
| 2005/0215977 A1 | 9/2005 | Uschold | |
| 2006/0025747 A1 | 2/2006 | Sullivan et al. | |
| 2006/0106360 A1 | 5/2006 | Wong | |
| 2006/0111667 A1 | 5/2006 | Matsurra et al. | |
| 2006/0157984 A1 | 7/2006 | Rome et al. | |
| 2006/0186045 A1 | 8/2006 | Jensen et al. | |
| 2007/0021725 A1 | 1/2007 | Villette | |
| 2007/0060841 A1 | 3/2007 | Henshaw | |
| 2007/0088313 A1 | 4/2007 | Zinger et al. | |
| 2007/0106244 A1 | 5/2007 | Mosler et al. | |
| 2007/0179441 A1 | 8/2007 | Chevallier | |
| 2007/0270759 A1 | 11/2007 | Pessin | |
| 2007/0270778 A9 | 11/2007 | Zinger et al. | |
| 2008/0045919 A1 | 2/2008 | Jakob et al. | |
| 2008/0103453 A1 | 5/2008 | Liversidge | |
| 2008/0103485 A1 | 5/2008 | Kruger | |
| 2008/0172039 A1 | 7/2008 | Raines | |
| 2008/0223484 A1 | 9/2008 | Horppu | |
| 2008/0287920 A1 | 11/2008 | Fangrow et al. | |
| 2008/0312634 A1 | 12/2008 | Helmerson et al. | |
| 2009/0254042 A1 | 10/2009 | Gratwohl et al. | |
| 2010/0137827 A1 | 6/2010 | Warren et al. | |
| 2010/0204671 A1 | 8/2010 | Kraushaar et al. | |
| 2010/0243099 A1 | 9/2010 | Yodfat | |

FOREIGN PATENT DOCUMENTS

| | | |
|---|---|---|
| DE | 2005519 | 10/1979 |
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0803267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| GB | 1579065 | 11/1980 |
| JP | 49-12690 | 5/1972 |
| JP | 288664 | 7/1990 |
| JP | 3030963 | 8/1996 |
| JP | 2000167022 | 6/2000 |
| JP | 2001505092 | 4/2001 |
| JP | 2001293085 | 10/2001 |
| TW | 482670 | 4/2002 |
| WO | WO 84/04672 | 12/1984 |
| WO | WO 84/04673 | 12/1984 |
| WO | WO 90/03536 | 4/1990 |
| WO | WO 98/19724 | 5/1998 |
| WO | WO 99/27886 | 6/1999 |
| WO | WO 99/62578 | 12/1999 |
| WO | WO 00/05292 | 2/2000 |
| WO | WO 00/35517 | 6/2000 |
| WO | WO 01/80928 | 11/2001 |
| WO | WO 02/02048 | 1/2002 |
| WO | WO 02/11794 | 2/2002 |
| WO | WO 02/064077 | 8/2002 |
| WO | WO 02/076540 | 10/2002 |
| WO | WO 2005/074860 | 8/2005 |
| WO | WO 2006/082350 | 8/2006 |
| WO | WO 2006/083333 | 8/2006 |
| WO | WO 2006/138184 | 12/2006 |
| WO | WO2008/028305 | 3/2008 |
| WO | WO 2008/115102 | 9/2008 |

OTHER PUBLICATIONS

Japan Application No. 2003-583539, Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009 (2 pages).

* cited by examiner

Fig. 12

CONNECTORS FOR FLUID CONTAINERS

TECHNICAL FIELD

The present invention concerns a connector for enabling fluid transfer between a first fluid container and a second fluid container, such as a syringe or needle protector. The present invention also concerns a fluid container comprising at least a part of such a connector.

BACKGROUND

Many medical connectors comprise a first component having a female luer-lock element that is arranged to be rigidly joined to a corresponding male luer-lock element of a second connector component that is attached to a medical line for example. The male luer lock element can thus be freely screwed into and unscrewed from the female luer-lock element. However, once the male luer-lock element has been screwed into the female luer-lock element of the connector, there is a risk that the connector components may be accidentally or inadvertently unscrewed, which could lead to the disconnection of the fluid line. This may entail a serious contamination risk for a patient and or any other person in the vicinity of the disconnected medical connector. Such a disconnection risk must especially be avoided when administering toxic fluid, such as cytostatic agents.

Some medical connectors are arranged so as to be non-disconnectable once they have been connected to a medical line for example. A disadvantage with such a connector is that it may induce an undesirable twist in the medical line when a second fluid container, such as a syringe or a needle protector, is secured to the connector in order to enable fluid transfer between the medical line and the second fluid container.

SUMMARY

An object of the invention is to overcome or ameliorate at least one of the disadvantages of the prior art, or to provide a useful alternative. A further object of the present invention is to provide a safe and reliable connector for enabling fluid between a first fluid container and a second fluid container, such as a syringe or needle protector.

At least one of these objects is achieved by a connector that comprises a first component that is arranged to be connected to a first fluid container and a second component that is arranged to be connected to a second fluid container. The first component is arranged to be non-rotatably connected to the second component, or a part of the second component, and to a first fluid container before a second fluid container is connected to the second component and/or before a first fluid container is connected to the first component. The connector comprises a locking and rotation-enabling element that is arranged to be activated once a second fluid container has been connected to the second component and/or once a first fluid container has been connected to the first element, which locking and rotation-enabling element enables the first component and the second component to rotate freely with respect to one another, i.e. rotate freely in one direction or a plurality of directions without hindrance, or to rotate freely in one direction or a plurality of directions for at least part of one revolution or any number of revolutions before it is prevented from rotating further. Once the locking and rotation-enabling element has been activated, it will not be possible to accidentally or inadvertently disconnect the first component from the second component, whereby the locking of the first and the second components is irreversible. According to an alternative embodiment of the present invention the first component is arranged to be disconnectable from the second component once the locking and rotation-enabling element has been activated, whereby the locking of the first and the second components is reversible.

The expressions "first fluid container" and "second fluid container" as used in this document are intended to mean any vessel that can at least temporarily contain a fluid, such as a vial, a medical line, a tube or an infusion fluid container, such as an infusion bottle or an infusion bag, a syringe or a needle protector device. The expression "a locking and rotation-enabling element that is arranged to be activated once a second fluid container has been connected to the second component and/or once a first fluid container has been connected to the first component" is intended to mean that the locking and rotation-enabling element is arranged to be activated either when one or both of the vessels that are to be connected to the connector. For example, if the locking and rotation-enabling element is arranged to be activated when it has been linearly, non-linearly or rotationally displaced a certain distance in for example the longitudinal direction of the connector, the connector may be arranged so that the connection of one or both of said vessels and/or the manual activation of a user may be required in order to displace the locking and rotation-enabling element the required distance.

It should be noted that the expression "the locking and rotation-enabling element" is intended to mean a single component or a plurality of components that are arranged to lock and to enable the rotation of the first component with respect to the second component.

The first and the second components of the connector according to the present invention may therefore be connected together so that they will not rotate with respect to each other until a second fluid container and/or a first fluid container is connected to the connector. On connection of a second fluid container and/or a first fluid container, the locking and rotation-enabling element will be activated and the first and the second components will then be able to rotate freely with respect to one another. The free rotation will clearly indicate to a user that a non-disconnectable connection has been made, i.e. that the first and the second components can not be separated without breaking the connector, using excessive force, or mis-using the connector. Furthermore, any undesired twists in the first fluid container or second fluid container may also be remedied by rotating the first and/or the second component of the connector.

According to an embodiment of the invention one of the first or second component comprises at least one protrusion that is arranged to become located in at least one corresponding cavity in the other of the first or second component or in the locking and rotation-enabling element, in order to connect the first component to the second component (or a part thereof) in a non-rotatable manner. The locking and rotation-enabling element is arranged to force the at least one protrusion out of the at least one corresponding cavity, whereby the first component and the second component are enabled to rotate freely with respect to one another when the at least one protrusion is forced out of the at least one corresponding cavity.

According to another embodiment of the invention the locking and rotation-enabling element is arranged to force the at least one protrusion out of the at least one corresponding cavity and into at least one slot, whereby the first component and the second component are enabled to rotate freely with respect to one another when the at least one protrusion is located in the at least one slot.

According to a further embodiment of the invention the locking and rotation-enabling element is arranged to be automatically activated when the second fluid container and/or first fluid container is/are connected to the connector. According to an embodiment of the invention the locking and rotation-enabling element is arranged to be automatically activated when it is directly or indirectly displaced by the second fluid container and/or the first fluid container when the second fluid container and/or the first fluid container is/are subsequently being connected to the connector, whereby the displacement of the locking and rotation-enabling element forces the at least one protrusion out of the at least one cavity.

Alternatively, in the connector according to the present invention the locking and rotation-enabling element is arranged to be manually activated by a user after the second fluid container and/or first fluid container has/have been connected to the connector. According to an embodiment of the invention the locking and rotation-enabling element is arranged to be manually activated by a user that directly or indirectly causes it to be displaced after the second fluid container and/or first fluid container has/have been connected to the connector, whereby the displacement of the locking and rotation-enabling element forces the at least one protrusion out of the at least one cavity.

According to another embodiment of the invention the connector comprises a snap fit mechanism to connect the first component to the second component. A snap fit mechanism is a self-locking joint whose mating parts exert a cam action, flexing until one part slips past a raised lip on the other part, preventing their separation.

According to a further embodiment of the invention the first component is arranged to be screwed into the second component. Alternatively, the first component is arranged to be slid into the second component.

According to an embodiment of the invention the first component and/or the second component comprises a membrane. The membrane of a second fluid container or a first fluid container may be pressed against the membrane of the connector component to form a double membrane and a piercing member, such as a needle, may then penetrate the double membrane in order to achieve leak free fluid transfer.

According to another embodiment of the present invention the connector comprises sealing means, such an o-ring or gasket, to ensure that a fluid-tight, leak-free connection is made between the first fluid container and the second fluid container.

The present invention also concerns a fluid container that comprises an integrally formed first component of a connector according to any of the embodiments of the invention. The connector according to the present invention may however be arranged to be connected to any fluid container.

In general, one aspect of the document features a connector for enabling fluid transfer between a first fluid container and a second fluid container, which connector comprises a first component that is arranged to be connected to a first fluid container and a second component that is arranged to be connected to a second fluid container, whereby the first component is arranged to be non-rotatably connected to the second component, or a part of the second component, and to a first fluid container before a second fluid container is connected to the second component and/or before a first fluid container is connected to the first component, characterized in that the connector comprises a locking and rotation-enabling element that is arranged to be activated once a second fluid container has been connected to the second component, and/ or once a first fluid container has been connected to the first component, which locking and rotation-enabling element enables the first component and the second component to rotate freely with respect to one another. One of the first or second components can comprise at least one protrusion that is arranged to become located in at least one corresponding cavity in the other of the first or second components or in the locking and rotation-enabling element, in order to connect the first component to the second component in a non-rotatable manner, and whereby the locking and rotation-enabling element is arranged to force the at least one protrusion out of the at least one corresponding cavity, whereby the first component and the second component are enabled to rotate freely with respect to one another when the at least one protrusion is forced out of the at least one corresponding cavity. The locking and rotation-enabling element can be arranged to force the at least one protrusion out of the at least one corresponding cavity and into at least one slot, whereby the first component and the second component are enabled to rotate freely with respect to one another when the at least one protrusion is located in the at least one slot. The locking and rotation-enabling element can be arranged to be automatically activated when the second fluid container is connected to the second component and/or once a first fluid container has been connected to the first component. The locking and rotation-enabling element can be arranged to be automatically activated when it is directly or indirectly displaced by the second fluid container when the second fluid container is subsequently being connected to the second component, whereby the displacement of the locking and rotation-enabling element forces the at least one protrusion out of the at least one cavity and/or when it is directly or indirectly displaced by the first fluid container when the first fluid container is subsequently being connected to the first component, whereby the displacement of the locking and rotation-enabling element forces the at least one protrusion out of the at least one cavity. The locking and rotation-enabling element can be arranged to be manually activated by a user after the second fluid container has been connected to the second component and/or when the first fluid container has been connected to the first component. The locking and rotation-enabling element can be arranged to be manually activated by a user that directly or indirectly causes it to be displaced after the second fluid container has been connected to the second component and/or the first fluid container has been connected to the first component, whereby the displacement of the locking and rotation-enabling element forces the at least one protrusion out of the at least one cavity. The connector can comprise a snap fit mechanism to connect the first component to the second component or the fluid enabling element. The first component can be arranged to be screwed into the second component. The first component can be arranged to be slid into the second component. The second component and/or the first component can comprise a membrane. The connector can comprise sealing means to ensure that a fluid-tight, leak-free connection is made between the first fluid container and the second fluid container.

In another aspect, this document provides a fluid container comprising an integrally formed first component of a connector. The connector can be configured as described herein.

BRIEF DESCRIPTION OF THE DRAWINGS

The present invention will hereinafter be further explained by means of non-limiting examples with reference to the appended schematic figures.

It should be noted that the drawings have not been drawn to scale and that the dimensions of certain features have been exaggerated for the sake of clarity.

DETAILED DESCRIPTION OF EMBODIMENTS

Figure 1:
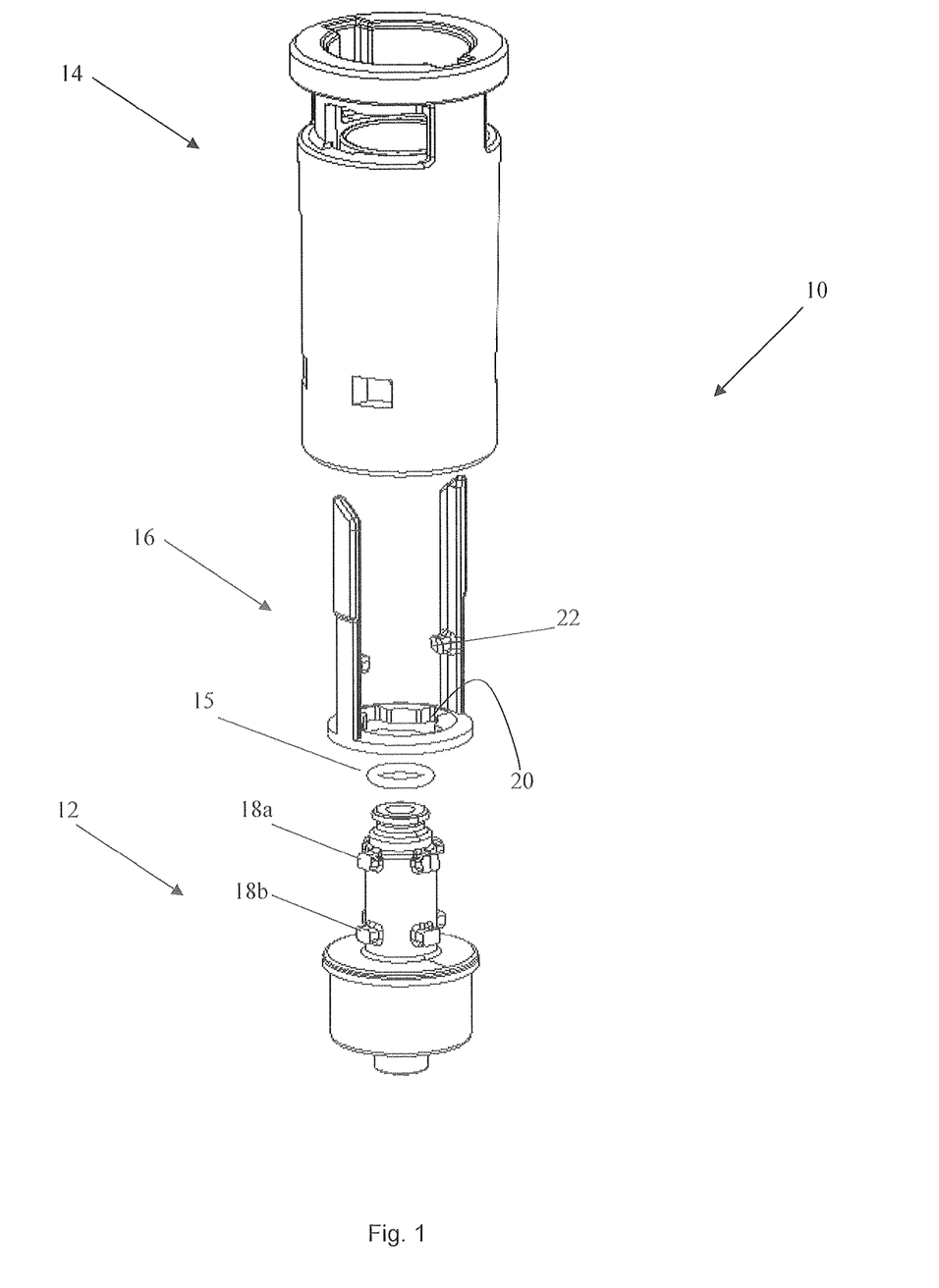
FIG. 1 shows an exploded view of a connector according to an embodiment of the invention.

FIG. 1 shows an exploded view of a connector 10 for enabling fluid transfer between a first fluid container and a second fluid container. The connector 10 comprises a first component 12 that is arranged to be connected to a first fluid container and a second component 14 that is arranged to be connected to a second fluid container. The first and the second component 12 and 14 in the illustrated embodiment are tubular and comprise at least one fluid channel (not shown) through which fluid may flow through the connector. The connector 10 comprises an o-ring 15 to ensure that a fluid-tight, leak-free connection is made between the first fluid container and the second fluid container.

The first component 12 is arranged to be non-rotatably connected to the second component 14 and to a first fluid container before a second fluid container is connected to the second component 14. The connector 10 comprises a locking and rotation-enabling element 16 that is arranged to be activated once a second fluid container has subsequently been connected to the second component 14. In the illustrated embodiment the locking and rotation-enabling element 16 constitutes part of the second component 14 and is non-rotatable, and slidably displaceable with respect to the second component 14. The locking and rotation-enabling element 16 enables the first component 12 and the second component 14 to rotate freely with respect to one another when it has been directly or indirectly activated (automatically or manually).

Figure 2:
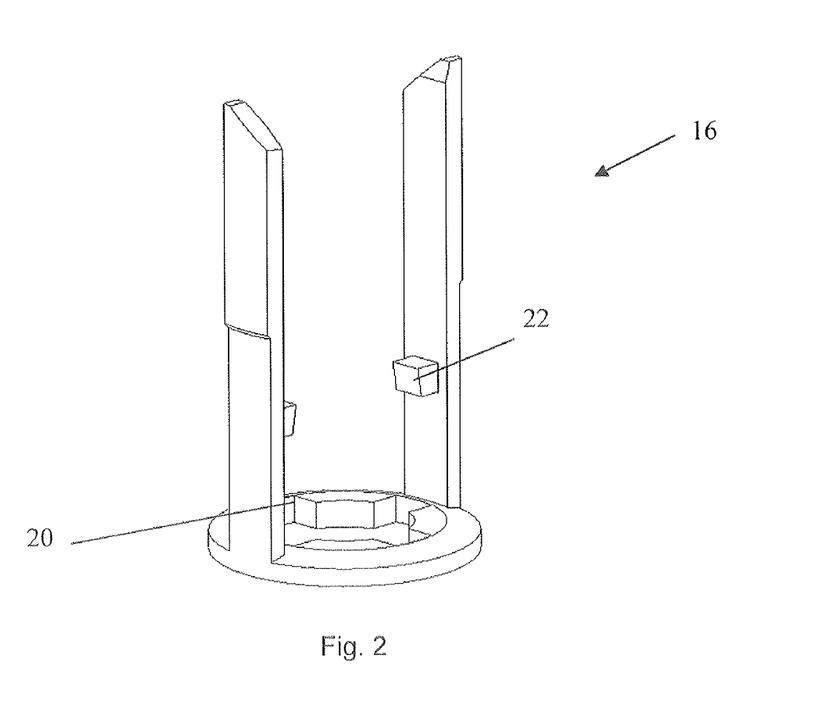
FIG. 2 depicts a locking and rotation-enabling element of a connector according to an embodiment of the invention.
Figure 3:
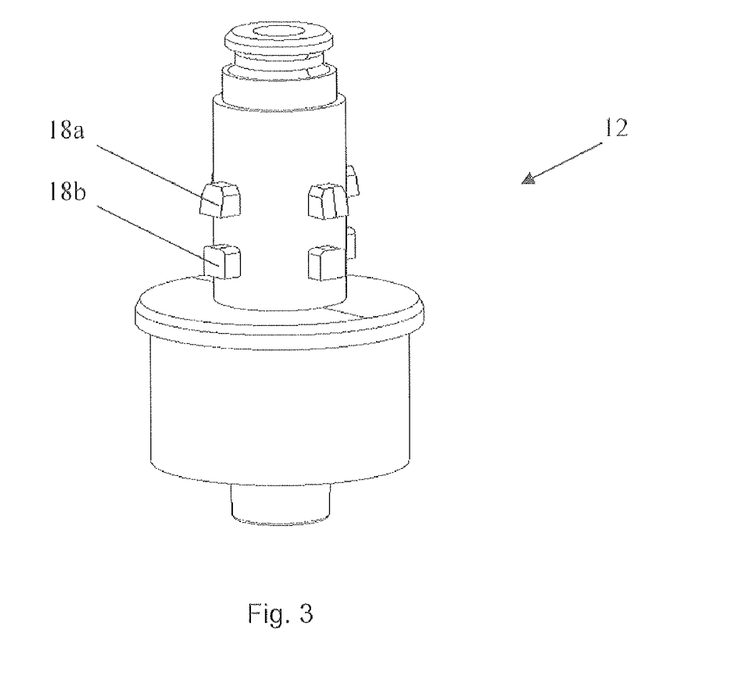
FIG. 3 shows a first component of a connector according to an embodiment of the invention.

With reference to FIGS. 1-3 the first component 12 comprises two levels of protrusions 18a and 18b. The lower level of protrusions 18b is arranged to become located in corresponding cavities 20 (whereby the turning force applied to the first component 12 will be transferred to the locking and rotation-enabling element 16) in the locking and rotation-enabling element 16 of the second component 14 in order to connect the first component 12 to the second component 14 in a non-rotatable manner. The upper level of protrusions 18a is arranged to become located adjacent to a row of protrusions 22 (shown in FIG. 1) on the locking and rotation-enabling element 16 in a snap fit manner for example.

Figure 4:
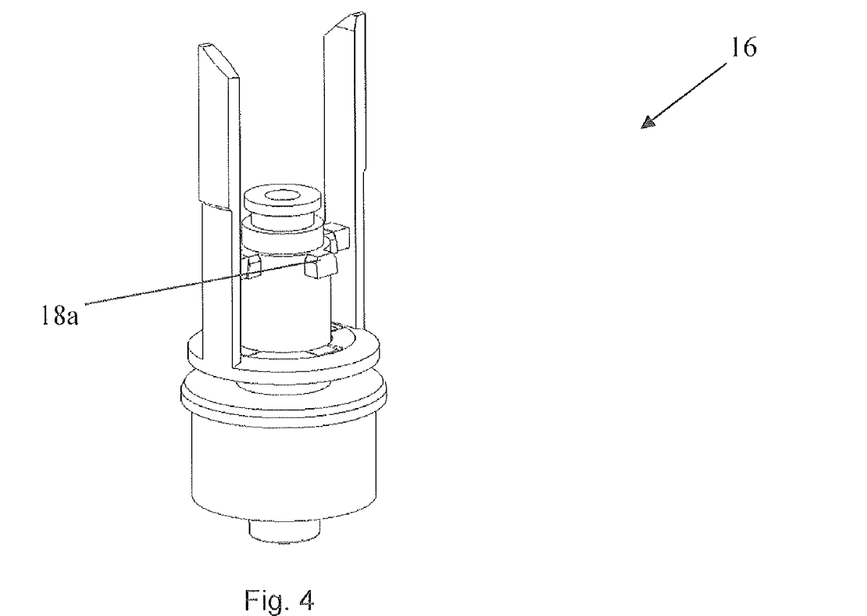
FIG. 4 shows a first component connected to a locking and rotation-enabling element in a non-rotatable manner.

FIG. 4 shows the first component 12 connected to the locking and rotation-enabling element 16, whereby the lower level of protrusions 18b is located in cavities 20 in the locking and rotation-enabling element 16.

Figure 5:
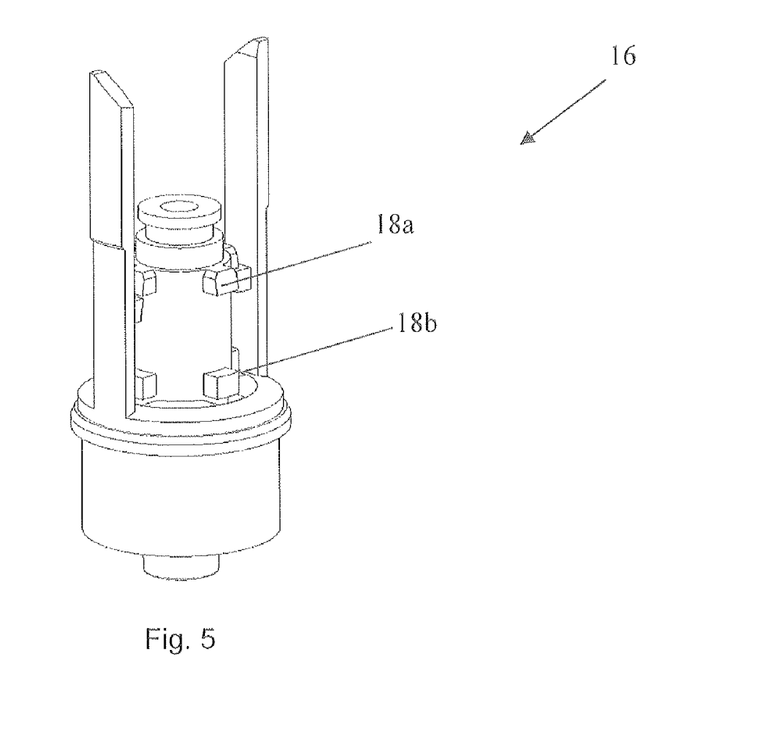
FIGS. 5 and 6 show a first component connected to a locking and rotation-enabling element in a manner that enables the first component to rotate freely with respect to the locking and rotation-enabling element.

When a second fluid container is connected to the second component 14 the locking and rotation-enabling element 16 will be slidably displaced downwards to the position shown in FIG. 5 and will force the lower level of protrusions 18b out of the cavities 20, whereby the first component 12 and locking and rotation-enabling element 16 (and consequently the second component 14) will then be able to rotate freely with respect to one another.

Figure 6:
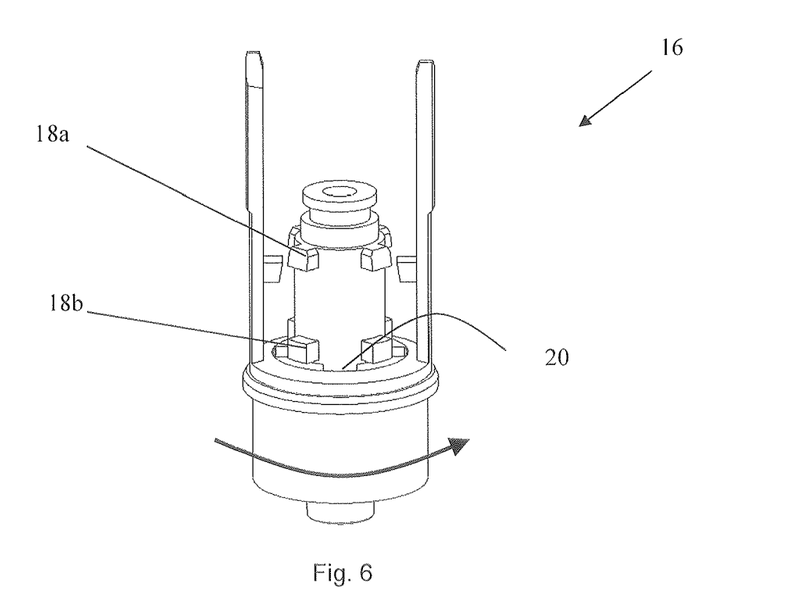

FIG. 6 shows the first component 12 in a position in which it has been rotated in the direction of the arrow in FIG. 6, whereby the cavities 20 in the locking and rotation-enabling element 16 are located slightly to the right of the lower level of protrusions 18b. It should be noted that the connector 10 may be arranged to also enable rotation in the direction opposite to the direction of the arrow in FIG. 6. According to an embodiment of the invention the connector 10 may comprise means to prevent the first component 12 and the second component 14 from returning to their unlocked position in which they cannot rotate with respect to one another. For example, in the embodiment illustrated in FIG. 6, the connector 10 may be provided with a spring-loaded mechanism to prevent the protrusions 18b from being displaced back into the cavities 20.

Figure 7:
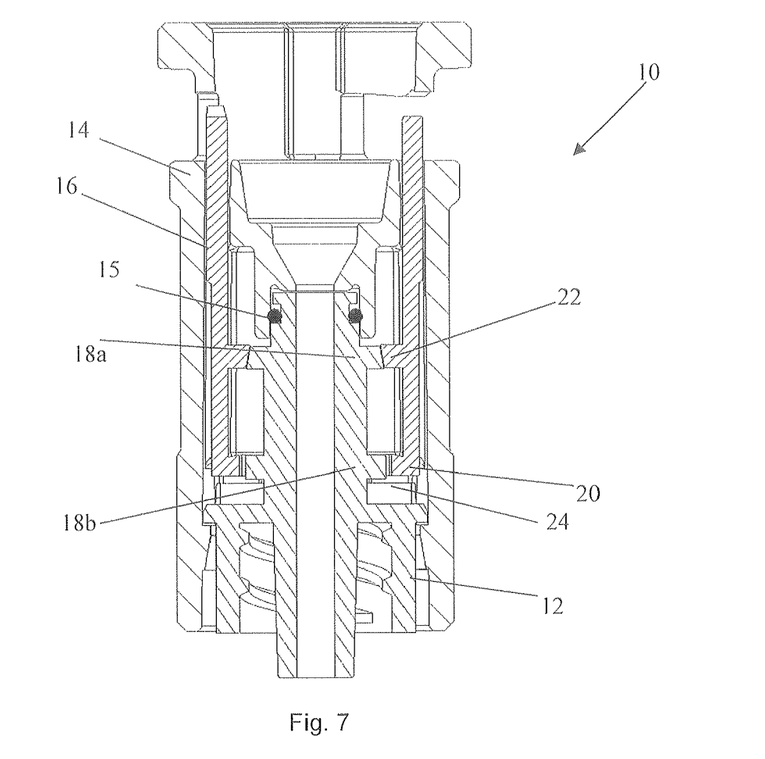
FIG. 7 shows a connector according to an embodiment of the invention in which a first and second component are connected in a non-rotatable manner.

FIG. 7 shows a cross section of the first component 12 and the second component 14 that includes the locking and rotation-enabling element 16, when the first component 12 and the second component 14 are connected in a non-rotatable manner with respect to one another, i.e. when the lower level of protrusions 18b is located in the cavities 20 in the locking and rotation-enabling element 16. The upper level of protrusions 18a rest against the protrusions 22 of the locking and rotation-enabling element 16. The connector shown in FIG. 7 comprises a slot 24 just below the lower level of protrusions 18b.

Figure 8:
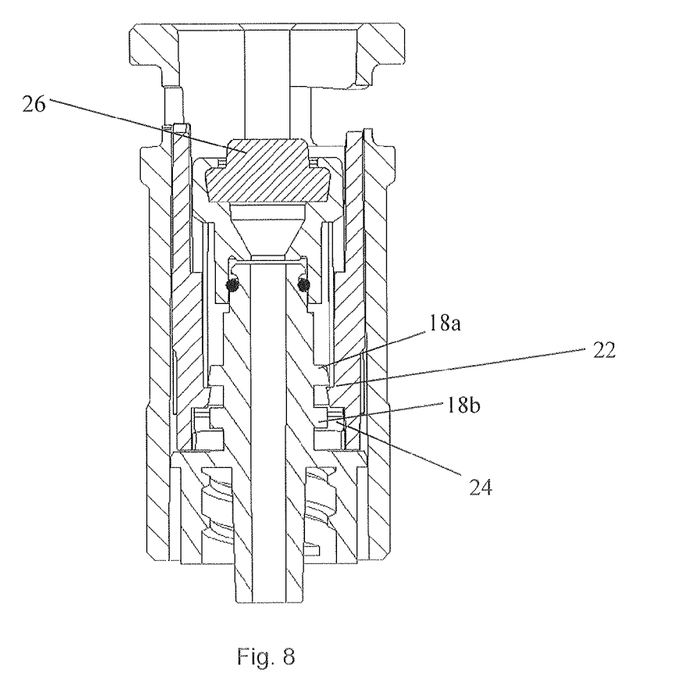
FIG. 8 shows a connector according to an embodiment of the invention in which a first and second component are connected in a rotatable manner.

When the locking and rotation-enabling element 16 is activated, it will be displaced downwards in FIG. 7 to the position shown in FIG. 8. In this position the lower level of protrusions 18b will become located in the slot 24 and the upper level of protrusions 18a will no longer rest against the protrusions 22 of the locking and rotation-enabling element 16. The first component 12 will therefore be able to rotate freely with respect to the locking and rotation-enabling element 16 and consequently with respect to the second component 14. Furthermore, since the protrusions 22 of the locking and rotation-enabling element 16 are now located between the upper and lower levels of protrusions 18a and 18b, the first component 12 will remain permanently connected to the second component 14 and will preferably not be separable therefrom without breaking the connector 10, using excessive force or misusing the connector 10. In the illustrated embodiment the second component 14 comprises a membrane 26 that may be placed in tight apposition against the membrane of a second fluid container, such as a needle protector, to ensure leak-free fluid transfer between the second fluid container and the second component 14.

In the connector embodiment shown in FIGS. 1-8, the locking and rotation-enabling element 16 is arranged to be directly and automatically activated when a second fluid container is connected to the second component 14. The connection of a second fluid container to the second component 14 namely causes the locking and rotation-enabling element 16 to be slidably displaced in a longitudinal direction (downwards in FIGS. 1-8) to enable the first component 12 to be freely rotatable with respect to the second component 14. Alternatively, such a slideable displacement may be achieved by a user manually activating a lever on the side of the connector for example once a second fluid container has been connected to the second component 14, which lever activates the locking and rotation-enabling element 16.

Figure 9:
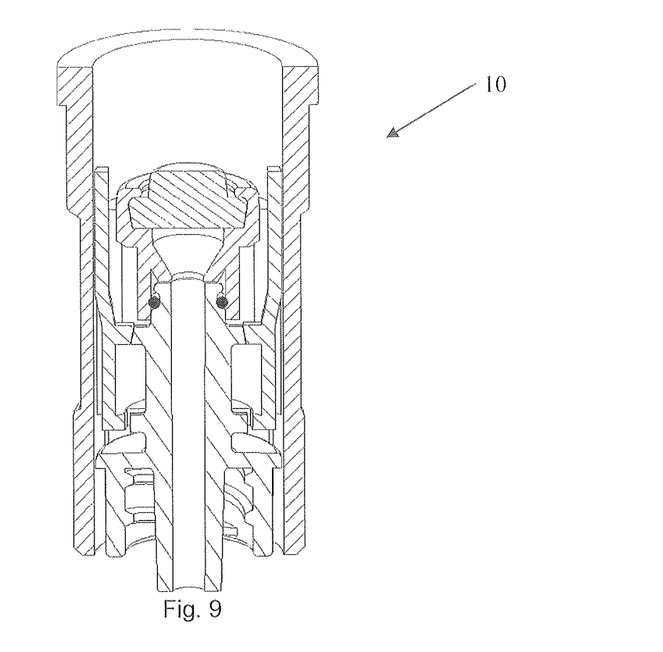
FIGS. 9 and 10 show a second component of connector according to different embodiments of the invention.
Figure 10:
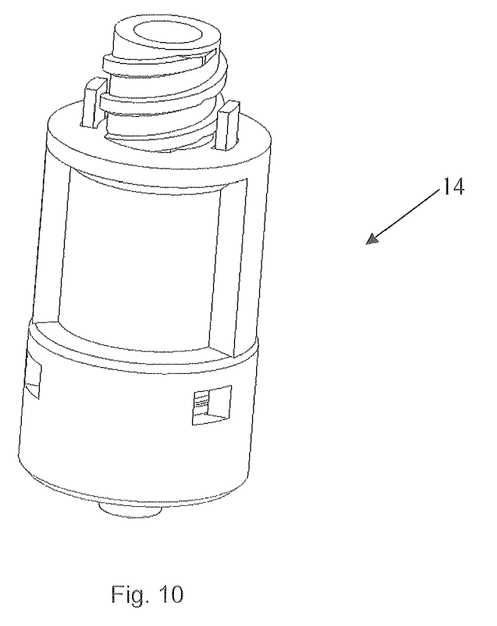

FIG. 9 shows a connector 10 comprising a snap fit mechanism 17. FIG. 10 shows that the second component 14 may be arranged to be screwed into a second fluid container. It should be noted that the first component 12 may also be arranged to be slid or screwed into a first fluid container. Furthermore, the first component 12 may be arranged to be slid or screwed into the second component 14 and the locking and rotation-enabling element 16 may be arranged to be displaced in a linear, non-linear or rotatable manner.

Figure 11:
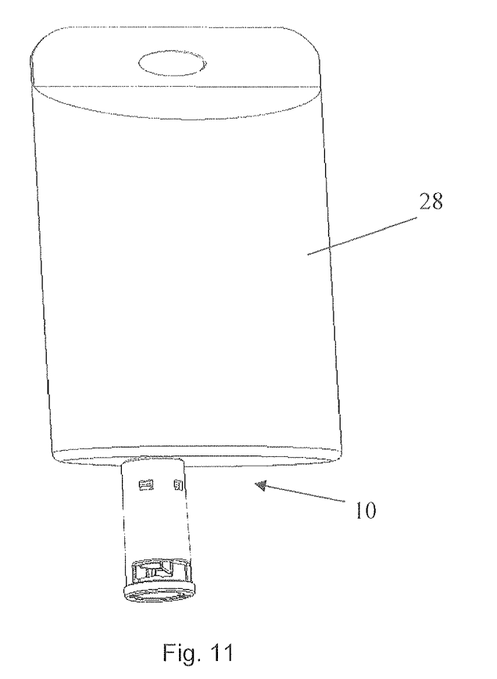
FIGS. 11 and 12 show a fluid container comprising at least a component of a connector according to the present invention.

FIG. 11 shows a first fluid container 28, namely an infusion bag, comprising an integrally formed connector 10 according to the present invention. Such a connector 10 may alternatively be arranged to be temporarily or permanently connected to the infusion port or the injection port of a standard infusion bag.

Figure 12:
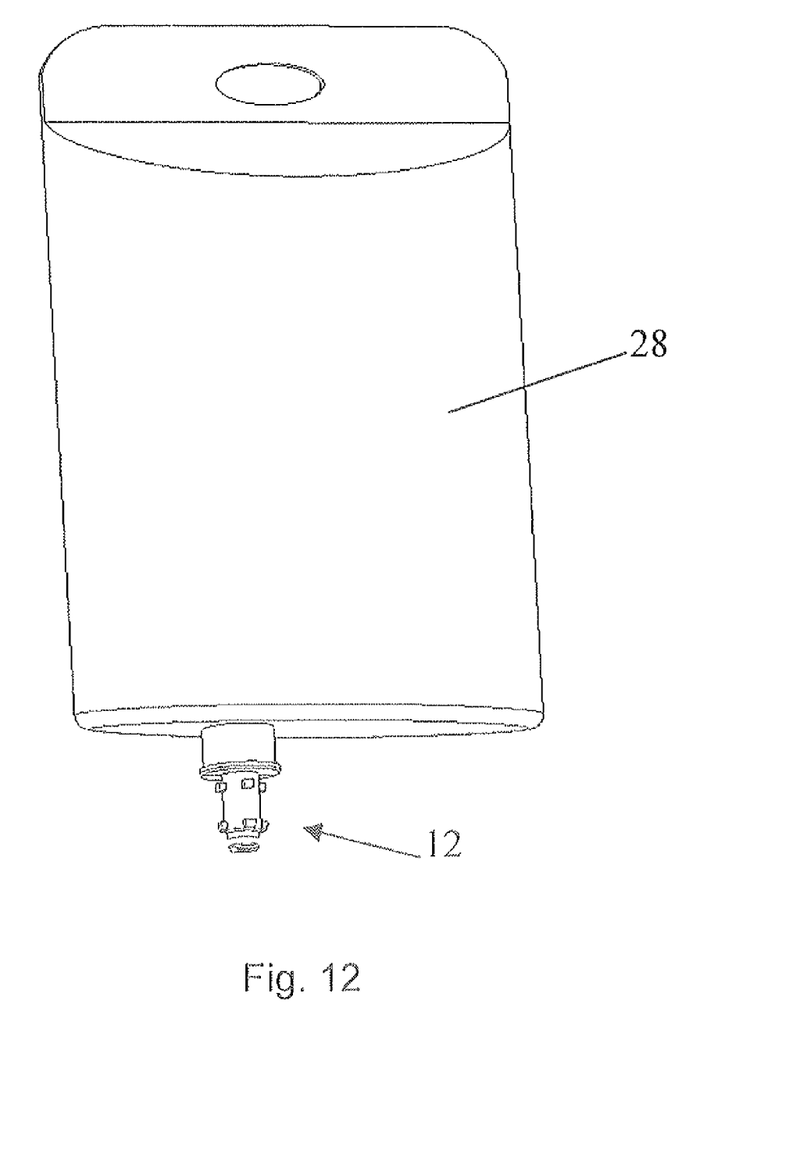

FIG. 12 shows a first fluid container 28, namely an infusion bag, comprising an integrally formed first component 12 of a connector 10 according to the present invention. Such a first component 12 may alternatively be arranged to be temporarily or permanently connected to the infusion port or the injection port of a standard infusion bag.

Further modifications of the invention within the scope of the claims would be apparent to a skilled person. For example, the first component 12 and the second component 14 may be connected between any two vessels between which fluid transfer is desired. The first component 12 may be arranged to be connected to the second component 14 (or a part thereof such as a locking and rotation-enabling element 16) in any suitable manner. There are many ways of designing and arranging a locking and rotation-enabling element 16 to enable free rotation between the first component 12 and the second component 14 of the connector 10 once a second fluid container and/or a medical container has/have been connected to the connector. The design and arrangement shown in the figures merely provides one such example in order to illustrate the principle of the present invention. Furthermore, it should be noted that although it is easier to manufacture a locking and rotation-enabling element 16 that is directly activated by the connection of a second fluid container and/or a first fluid container to the connector 10, the connector may be provided with an additional mechanism to indirectly automatically or manually activate the locking and rotation-enabling element 16.

What is claimed is:

1. A connector for enabling fluid transfer between a first fluid container and a second fluid container, which connector comprises a first component that is arranged to be connected to a first fluid container and a second component that is arranged to be connected to a second fluid container, whereby said first component is arranged to be non-rotatably connected to said second component, or a part of the second component, and to a first fluid container before a second fluid container is connected to said second component or before a first fluid container is connected to the first component, wherein said connector comprises a locking and rotation-enabling element that is arranged to be activated once a second fluid container has been connected to said second component, or once a first fluid container has been connected to the first component, which locking and rotation-enabling element enables the first component and the second component to rotate freely with respect to one another.

2. The connector of claim 1, wherein one of said first or second components comprises at least one protrusion that is arranged to become located in at least one corresponding cavity in the other of said first or second component or in said locking and rotation-enabling element, in order to connect said first component to said second component in a non-rotatable manner, and whereby said locking and rotation-enabling element is arranged to force said at least one protrusion out of said at least one corresponding cavity, whereby said first component and said second component are enabled to rotate freely with respect to one another when said at least one protrusion is forced out of said at least one corresponding cavity.

3. The connector of claim 2, wherein said locking and rotation-enabling element is arranged to force said at least one protrusion out of said at least one corresponding cavity and into at least one slot, whereby said first component and said second component are enabled to rotate freely with respect to one another when said at least one protrusion is located in said at least one slot.

4. The connector of claim 3, wherein said locking and rotation-enabling element is arranged to be automatically activated when said second fluid container is connected to said second component or once a first fluid container has been connected to the first component.

5. The connector of claim 4, where said locking and rotation-enabling element is arranged to be automatically activated when it is directly or indirectly displaced by said second fluid container when said second fluid container is subsequently being connected to said second component, whereby said displacement of said locking and rotation-enabling element forces said at least one protrusion out of said at least one cavity or when it is directly or indirectly displaced by said first fluid container when said first fluid container is subsequently being connected to said first component, whereby said displacement of said locking and rotation-enabling element forces said at least one protrusion out of said at least one cavity.

6. The connector of claim 1, wherein said locking and rotation-enabling element is arranged to be automatically activated when said second fluid container is connected to said second component or once a first fluid container has been connected to the first component.

7. The connector of claim 1, wherein said locking and rotation-enabling element is arranged to be manually activated by a user after said second fluid container has been connected to said second component or when said first fluid container has been connected to said first component.

8. The connector of claim 3, wherein said locking and rotation-enabling element is arranged to be manually activated by a user after said second fluid container has been connected to said second component or when said first fluid container has been connected to said first component.

9. The connector of claim 8, wherein said locking and rotation-enabling element is arranged to be manually activated by a user that directly or indirectly causes it to be displaced after said second fluid container has been connected to said second component or said first fluid container has been connected to said first component, whereby said displacement of said locking and rotation-enabling element forces said at least one protrusion out of said at least one cavity.

10. The connector of claim 1, wherein said connector comprises a snap fit mechanism to connect said first component to said second component or said fluid enabling element.

11. The connector of claim 1, wherein said first component is arranged to be screwed into said second component.

12. The connector of claim 1, wherein said first component is arranged to be slid into said second component.

13. The connector of claim 1, wherein said second component or said first component comprise a membrane.

14. The connector of claim 1, wherein said connector comprises sealing means to ensure that a fluid-tight, leak-free connection is made between the first fluid container and the second fluid container.

15. A fluid container comprising an integrally formed first component of a connector for enabling fluid transfer between said fluid container and a second fluid container, which connector comprises a second component that is arranged to be connected to said second fluid container, whereby said first component is arranged to be non-rotatably connected to said second component, or a part of the second component, and to said fluid container before said second fluid container is connected to said second component, wherein said connector comprises a locking and rotation-enabling element that is arranged to be activated once said second fluid container has been connected to said second component, which locking and rotation-enabling element enables the first component and the second component to rotate freely with respect to one another.

* * * * *